United States Patent [19]

Jung et al.

[11] Patent Number: 4,965,385
[45] Date of Patent: Oct. 23, 1990

[54] ORGANOSILANE STABILIZERS FOR INORGANIC SILICATES IN ANTIFREEZER/COOLANT COMPOSITIONS

[75] Inventors: Il Nam Jung; Sang Yo Hwang; Hae Kyung Bae, all of Seoul, Rep. of Korea

[73] Assignee: Korea Advanced Institute of Science and Technology, Seoul, Rep. of Korea

[21] Appl. No.: 180,489

[22] Filed: Apr. 12, 1988

[30] Foreign Application Priority Data

Dec. 22, 1987 [KR] Rep. of Korea .............. 14733/1987

[51] Int. Cl.$^5$ .............................................. C07F 7/10
[52] U.S. Cl. ................................... 556/416; 556/417; 556/445
[58] Field of Search ............... 556/416, 417, 445, 449, 556/437, 436, 441

[56] References Cited

U.S. PATENT DOCUMENTS 4,230,904 3/1988 Pauluth et al. ...................... 556/416

FOREIGN PATENT DOCUMENTS 862779 2/1971 Canada ................................. 556/416

Primary Examiner—Gary P. Straub
Assistant Examiner—Stuart L. Hendrickson
Attorney, Agent, or Firm—Darby & Darby

[57] ABSTRACT

Organotrialkoxysilane stabilizers for inorganic silicate corrosion inhibitor additives in antifreezer/coolant formulations are described. The stabilizers have the following structure:

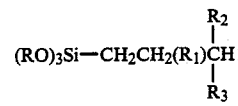

wherein R is an alkyl group of 1-4 carbon atoms, $R_1$ is either

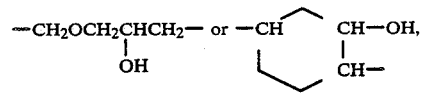

and $R_2$ and $R_3$ may be same or different and selected from —Ph, —CN,

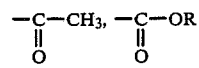

(wherein R is an alkyl group of 1-4 carbon atoms). These stabilizers help prevent the gelation of the corrosion inhibiting silicate additives in antifreezer/coolant formulations so that the silicates could be more persistent in their corrosion inhibiting properties.

6 Claims, No Drawings

ORGANOSILANE STABILIZERS FOR INORGANIC SILICATES IN ANTIFREEZER/COOLANT COMPOSITIONS

BACKGROUND OF THE INVENTION

1. Field of the Invention

The present invention relates to organosilicon compounds having hydroxyl and carboxyl groups or cyano group which are effective stabilizers for aqueous silicates, silica sols and other silica containing water, such as boiler water, antifreezer and coolant solutions.

2. Descriptions of the Prior Art

It is well known that alkali metal silicates are effective metal corrosion inhibitor. It has therefore been desirable to use alkali metal silicates in antifreezer and coolant formulations. However, antifreezer and coolant compositions containing such silicates generally have the tendency to gel or form precipitates during the storage or after prolonged use at elevated temperatures. Thus, it has been previously proposed to use a stabilizer to prevent the gelation of the alkali metal silicates in the antifreezer compositions so that the silicates could be more persistent in their corrosion inhibiting properties.

A number of organosilicon compounds and organosilicon polymers or organosilicon copolymers with organic polymers such as polyethylene oxides have been known to be effective as the stabilizers for alkaline metal silicates corrosion inhibitor additives in antifreezer/coolant compositions.

U.S. Pat. Nos. 4,462,921, 4,287,077 and 4,485,025 disclose the use of organosilicon polymers or copolymers with organic polymer as the stabilizers for this purpose. Since the organic polymers have limited solubility in aqueous systems or in glycols, they are usually coupled with hydrophilic groups such as carboxylic acids, polyethers etc. Nonhydrolyzable linkage between the hydrophilc groups and organosilicon polymers can be obtained by hydrosilylation reaction. (Y. Lukevit M. G. Voronkov, "Organic Insertion Reactions of Group IV Elements", Consulant Bureau, New York, 1966). Unfortunately the reaction requires expensive platinum catalyst. In U.S. Pat. No. 4,514,315, there is disclosed that an aqueous or alcohol solution of a alkylene silane grafted polyether provides an aluminum corrosion inhibitor effect.

Organotrialkoxysilanes have been used in antifreeze compositions to improve the anti-gel characteristics of those compositions. U.S. Pat. Nos. 3,198,820, 3,265,623 and 3,312,622 disclose the use of organic acid silane compounds for this purpose. U.S. Pat. Nos. 3,203,969 and 3,248,329 also disclose the use of aminosilane compounds for this purpose. In U.S. Pat. Nos. 4,333,843 and 4,367,154, there is disclosed that the self life or gelation resistance of single phase aqueous glycol or glycol ether compositions can be improved by the addition to the glycol compositions of an effective amount of the hydrolyzate of organophosphorous-silicon compounds.

Pines et al described another system in U.S. Pat. Nos. 3,337,496 and 3,341,469 that was found useful for inhibiting corrosion in aqueous alcohol compositions. It consisted of a mixture of hydroxyalkylsilanes or hydroxyalkylether silanes and a silicate. The materials are stated as being remarkably soluble in aqueous liquids. The hydroxyalkylsilanes and hydroxyalkylether silanes were easily prepared by hydrolysis of the corresponding epoxyalkylsilanes in the presence of base.

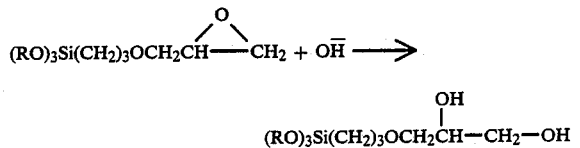

SUMMARY OF THE INVENTION

The invention concerns organotrialkoxysilane stabilizers for inorganic silicate corrosion inhibitor additives in antifreezer/coolant formulations. The stabilizers have the following structure;

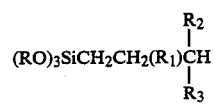

Wherein R is an alkyl group of 1–4 carbon atoms, $R_1$ is either

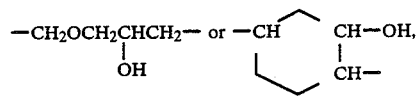

and $R_2$ and $R_3$ may be same or different and selected from —CN,

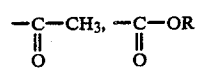

(wherein R is an alkyl group of 1–4 carbon atoms)

DETAILED DESCRIPTION OF THE INVENTION

The glycols such as ethylene glycol, diethylene glycol, propylene glycol, and dipropylene glycol can be used as major components in the present composition. The glycol ethers such as the methyl, ethyl, propyl, and butyl ether of ethylene glycol are also useful. Ethylene glycol is particularly preferred as the major antifreeze composition component.

Numerous corrosion inhibitors for antifreeze compositions have been proposed to date. Such inhibitors include both organic materials and inorganic materials. Illustrative of the organic materials that have been used as inhibitors in anti-freeze compositions are: guonidine, citrates, coal tar derivatives, petroleum bases, thiocyanates, peptones, phenols, thioureas, tannin, quinoline, morpholine, triethanolamine, tatarates, glycol monoricinoleate, organic nitrites, mercaptans, organic oils, sulfonated hydrocarbons, fatty oils and soaps. Illustrative of the inorganic materials that have been used as inhibitors are: sulfates, sulfides, fluorides, the alkali metal chromates, nitrites, phosphates, borates, tungstates, molybdates, carbonates, and silicates.

A number of known corrosion inhibitor and additives can be used in the present invention. The most preferred corrosion inhibitors are the alkali metal silicates, such as sodium metasilicate, potassium metasilicate and lithium metasilicate. Other corrosion inhibitors and additives may be used, such as alkali metal borates which include sodium tetraborate, potassium tetraborate and sodium metaborate. Other permissible component include alkali metal mercaptobenzotriazoles, alkali metal polytriazoles, alkali metal vanadates, alkali metal molybdates, and alakli metal nitrates such as sodium nitrate and potassium nitrate, alakli metal nitrites such as sodium and potassium nitrite, alkali metal phosphates such as sodium and potassium phosphate, alkali metal benzoates and various antifoaming agents and dyes, if desired.

The stabilizers useful in the invention are organotrialkoxysilanes which have carbonyl or carboxyl groups and the solublizing hydroxyl group. Gelation resistant additive compounds of this type may be prepared by reacting commercially available epoxy substituted coupling agents such as gamma-glycidoxypropyltrimethoxysilane and beta-(3,4-epoxycyclohexyl) ethyltrimethoxy-silane with the compounds of general formula 1 in the presence of base catalyst such as alkyllithiums, sodium hydride, Grignard reagents, and alkaline metal alkoxides.

General formula 1:

X—CH$_2$—Y wherein

X and Y may be same or different and selected from a functional group of the class of —Ph, —CN,

—COOR(wherein R is an alkyl group of 1–4 carbon atoms).

The compound of general formula 1 have two acidic protons at alpha position which can be easily pulled off by the base. The resulting carbanions attack the epoxide ring to open up the ring and form a new carbon-carbon bond. This gives a alkoxide anion which will pick up the proton at alpha position to generate another carbanion. This is why only catalytic amount of base is required to complete the reaction. Although this reaction goes smoothly at room temperature, it will speed up at the elevated temperature. At the elevated temperature alkoxy groups on silicon may be reacted to form a dimers or oligomers as the byproducts. However, the contaminated byproducts do not significantly lower the antigel activity of the products.

nal silicate. Thus, the silicate remains in solution in the antifreeze composition. It is theorized that the silanol formed polymerizes in some way, but it is unclear whether the silanol polymerizes with itself or whether it copolymerizes with the silicate. The important thing is that the silicate stays in solution and the part of the silicate which exhibits corrosion inhibition activity retains this activity.

The amounts of corrosion inhibitors discussed above known to be effective are well known in the art. Of course, the amount will vary for each inhibitor. It is not possible to set forth exactly the amount of silicate to be used in each instance due to the complicating influence of the other corrosion inhibitors such as the aforementioned borates, triazoles, nitrates, nitrites and phosphates. Simple, accelerated aging tests can be used to determine the amount of silicate which when added will give the desired corrosion resistance. Generally, the proportion of silicates should range from about 0.025 to 1.0 percent by weight, preferably about 0.05 to 0.5 percent by weight.

The gelation resistant organosiloxane compound should be used at levels of about 100 to 10,000 ppm to prevent gelation of the inorganic silicates in antifreeze/coolant formulations. These limits are generally much lower than those found in much of the prior art.

Throughout this specification it is noted that the gellation inhibitor is first created and subsequently added to the alkylene glycol composition. However, an alternate approach, which may even turn out to be the preferred one in practice, is to form the gelation inhibitor in situ. The invention relates to a glycol composition containing these gelation inhibitors and is not restricted by the method by which this is accomplished.

This invention will be further illustrated by the following examples which are not intended to limit the invention, but rather to illuminate it.

EXAMPLE 1

To a one liter, three neck, round bottomed flask equipped with a mechanical stirrer, a dropping funnel, and a reflux condenser was placed 160 g(1 mole) of diethylmalonate under the dry nitrogen atmosphere. With stirring, 60 ml(about 0.1 mole) of 1.6M n-butyllithium solution in hexane was added dropwise through the dropping funnel. At this time the evolution of butane gas was observed by means of a mineral filled

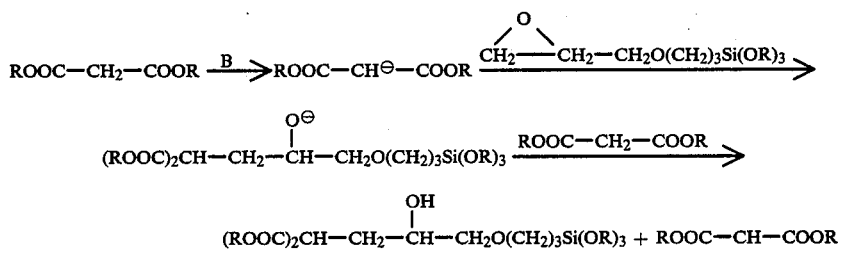

The improvement in the anti-gel characteristics of the antifreeze compositions of the present invention is achieved because of the chemical reaction between the various silanol and silicate components of the composition. When the organosilane is added to a silicate containing antifreeze composition, it is hydrolyzed by the water present to form the corresponding silanol. The silanol reacts with the silicate in the composition to form a reaction product which is much more stable with respect to gel and precipitate formations than the origibubbler conected to the top of the condenser and white solids precipitated, as the reaction proceeded. When no further gas evolution was stopped, 236 g(1 mole) of glycidoxypropyltrimethoxysilane was added dropwise for 2 hrs. The solid was dissolved and the solution turned to light yellow. The solution was refluxed to complete the reaction for another 30 minutes. Gas chromatography analysis showed that no reactants were left.

The solvent of hexane was evaporated to give the product.

The product contained about 10% of lithium salt of the product. Since the salt reacts with water to give the product back, it was not necessary to remove the salt from the product before the usage as the stabilizer for the inorganic slicates in antifreeze formulation.

| ir | OH | 3410 cm$^{-1}$ |
|---|---|---|
|  | C=O | 1782 cm$^{-1}$ |
| nmr($\delta$) | 0.46 (m, 2H), Si—CH$_2$ | |
|  | 1.23 (t, 6H), CH$_3$ | |
|  | 1.67 (m, 4H), C—CH$_2$—C | |
|  | 2.27 (m, 1H), C—CH—C<br>             \|<br>             C | |
|  | 2.62 (m, 1H), C—CH—C<br>             \|<br>             OH | |
|  | 3.51 (m, 4H), C—CH$_2$—OH | |
|  | 3.53 (s, 9H), (CH$_3$O)$_3$ Si | |
|  | 3.75 (t, 4H), O—CH$_2$—C | |
|  | 4.88 (m, 1H), —OH | |

EXAMPLE 2

The product was prepared using the same procedure as described in Example 1 except n-butyllithium was replaced by 0.1 moles of Na-H dispersed in 50 ml of dry THF solution.

EXAMPLE 3

The product was prepared using the same procedure as described in Example 1 except n-butyllithium was replaced by 0.1 moles of methylmagnesiumchloride in THF.

EXAMPLE 4

The product was prepared using the same procedure as described in Example 1 except n-butyllithium was replaced by 0.1 moles of sodium methoxide in methanol solution.

EXAMPLE 5

The procedure of Example 1 was repeated using beta-(3,4-epoxycyclohexyl)ethyltrimethoxysilane instead of glycidoxypropyltrimethoxysilane.

| ir | OH | 3420 cm$^{-1}$ |
|---|---|---|
|  | C=O | 1736 cm$^{-1}$ |
| nmr($\delta$) | 0.43 (m, 2H), Si—CH$_2$ | |
|  | 1.12 (t, 6H), CH$_3$ | |
|  | 1.15–2.18 (m, 18H), C—CH$_2$—C, C—CH—C<br>                                                  \\<br>                                                   C | |
|  | 3.42 (s, 9H), CH$_3$O— | |
|  | 3.66 (m, 5H), O—CH$_2$—C, C—CH—C<br>                                             \|\|<br>                                             O | |
|  | 4.10 (m, 1H), OH | |

EXAMPLE 6

The product was prepared using the same procedure as described in Example 5 except n-butyllithium was replaced by 0.1 moles of Na-H dispersed in 50 ml of dry THF solution.

EXAMPLE 7

The product was prepared using the same procedure as described in Example 5 except n-butyllithium was replaced by 0.1 moles of methylmagnesiumchloride in THF.

EXAMPLE 8

The product was prepared using the same procedure as described in Example 5 except n-butyllithium was replaced by 0.1 moles of sodium methoxide in methanol solution.

EXAMPLE 9

To a one liter, three neck, round bottomed flask equipped with a mechanical stirrer, a dropping funnel, and a reflux condenser was placed 113 g (1 mole) of ethylcyanoacetate under the dry nitrogen atmosphere. With stirring, 60 ml (about 0.1 mole) of 1.6M n-butyllithium solution in hexane was added dropwise through the dropping funnel. Butane gas was evolved and white solids precipitated, as the reaction proceeded. When the gas evolution was stopped, 236 g (1 mole) of glycidoxypropyltrimethoxysilane was added dropwise for 2 hrs. The solid was dissolved and the solution turned to light yellow. The solution was refluxed to complete the reaction for another 2 hrs. Gas chromatography analysis showed that no reactants were left. The solvent of hexane was evaporated to give the product.

The product contained about 10% of lithium salt of the product. Since the salt reacts with water to give the product back. It was not necessary to remove the salt from the product before the usage as the stabilizer for the inorganic silicates in antifreeze formulation.

| ir | OH | 3436 cm$^{-1}$ |
|---|---|---|
|  | CN | 2175 cm$^{-1}$ |
|  | C=O | 1770 cm$^{-1}$ |
|  |  | 1680 cm$^{-1}$ |
| nmr($\delta$) | 0.43 (m, 2H), Si—CH$_2$ | |
|  | 1.18 (t, 3H), C—CH$_3$ | |
|  | 1.57 (m, 2H), C—CH$_2$—C | |
|  | 2.42 (m, 1H), C—CH—C<br>                                    \|<br>                                    C | |
|  | 2.77 (m, 1H), C—CH—CN | |
|  | 3.30–3.52 (m, 6H), C—CH$_2$—O | |
|  | 3.45 (s, 9H), CH$_3$O— | |
|  | 3.72 (q, 2H), O—CH$_2$—C | |
|  | 4.63 (m, 1H), OH | |

EXAMPLE 10

The product was prepared using the same procedure as described in Example 9 except n-butyllithium was replaced by 0.1 moles of Na-H dispersed in 50 ml of dry THF solution.

EXAMPLE 11

The product was prepared using the same procedure as described in Example 9 except n-butyllithium was replaced by 0.1 moles of methylmagnesiumchloride in THF.

EXAMPLE 12

The product was prepared using the same procedure as described in Example 9 except n-butyllithium was replaced by 0.1 moles of sodium methoxide in methanol solution.

EXAMPLE 13

To a one liter, three neck, round bottomed flask equipped with a mechanical stirrer, a dropping funnel, and a reflux condenser was placed 113 g (1 mole) of ethylcyanoacetate under the dry nitrogen atmosphere. With stirring, 60 ml (about 0.1 mole) of 1.6M n-butyllithium solution in hexane was added dropwise through the dropping funnel. Butane gas was evolved and white solids precipitated, as the reaction proceeded. When the gas evolution was stopped, 246 g (1 mole) of beta-(3,4-epoxycyclohexyl)trimethoxysilane was added dropwise for 2 hrs. The solid was dissolved and the solution turned to light yellow. The solution was refluxed at 120° C. to complete the reaction for another 4 hrs. Gas chromatography analysis showed that no reactants were left. The solvent of hexane was evaporated to give the product.

The product contained about 10% of lithium salt of the product. Since the salt reacts with water to give the product back. It was not necessary to remove the salt from the product before the usage as the stabilizer for the inorganic silicates in antifreeze formulation.

| ir | OH | 3430 cm$^{-1}$ |
| --- | --- | --- |
|  | CN | 2172 cm$^{-1}$ |
|  | C=O | 1774 cm$^{-1}$ |
|  |  | 1727 cm$^{-1}$ |
| nmr($\delta$) | 0.67 (m, 2H), Si—CH$_2$ | |
|  | 1.23 (t, 3H), C—CH$_3$ | |
|  | 1.67 (m, 2H), si—C—CH$_2$—C | |
|  | 2.11 (s, 1H), CNCH— | |
|  | 2.40–2.47 (m, 4H), C—CH—C | |
|  | 3.34–3.39 (m, 4H), CH$_2$—O | |
|  | 3.61 (s, 9H), CH$_3$O— | |
|  | 3.88 (q, 2H), O—CH$_2$—C | |
|  | 4.63 (m, 1H), OH | |

EXAMPLE 14

The product was prepared using the same procedure as described in Example 13 except n-butyllithium was replaced by 0.1 moles of Na-H dispersed in 50 ml of dry THF solution.

EXAMPLE 15

The product was prepared using the same procedure as described in Example 13 except n-butyllithium was replaced by 0.1 moles of methylmagnesiumchloride in THF.

EXAMPLE 16

The product was prepared using the same procedure as described in Example 13 except n-butyllithium was replaced by 0.1 moles of sodium methoxide in methanol solution.

EXAMPLE 17

The procedure of example 1 was repeated using the same number of moles of ethylacetoacetate instead of dimethylmalonate to prepare the stabilizer.

| ir | OH | 3457 cm$^{-1}$ |
| --- | --- | --- |
|  | C=O | 1727 cm$^{-1}$ |
|  |  | 1774 cm$^{-1}$ |
| nmr($\delta$) | 0.43 (m, 2H), Si—CH$_2$ | |
|  | 1.18 (t, 3H), C—CH$_3$ | |
|  | 1.62 (m, 4H), C—CH$_2$—C | |
|  | 2.21 (s, 3H), O=CH$_3$ | |
|  | 2.45 (m, 1H), C—CH—C (C) | |
|  | 2.63 (m, 1H), C—CH—C (OH) | |
|  | 3.55 (s, 9H), CH$_3$O— | |
|  | 3.62 (m, 4H), CH$_2$—O—CH$_2$ | |
|  | 3.90 (q, 2H), O—CH$_2$—C | |
|  | 4.53 (m, 1H), OH | |

EXAMPLE 18

The procedure of example 1 was repeated using the same number of moles of methylphenylacetate instead of dimethylmalonate to prepare the stabilizer.

| ir | OH | 3427 cm$^{-1}$ |
| --- | --- | --- |
|  | C=O | 1750 cm$^{-1}$ |
|  |  | 1792 cm$^{-1}$ |
| nmr($\delta$) | 0.50 (m, 2H), Si—CH$_2$ | |
|  | 1.65 (m, 4H), C—CH$_2$—C | |
|  | 2.65 (m, 1H), C—CH—C (O) | |
|  | 3.50 (s, 9H), CH$_3$O—Si | |
|  | 3.60 (m, 5H), CH$_2$—O—CH$_2$, Ph—CH— | |
|  | 3.75 (s, 3H), O—CH$_3$ | |
|  | 4.62 (m, 1H), OH | |
|  | 7.25 (m, 5H), C$_6$H$_5$ | |

EXAMPLE 19

To a one liter, three neck, round bottomed flask equipped with a mechanical stirrer, a dropping funnel, and a reflux condenser was placed 160 g (1 mole) of benzylcyanide under the dry nitrogen atmosphere. With stirring, 60 ml (about 0.1 mole) of 1.6M n-butyllithium solution in hexane was added dropwise through the dropping funnel. Butane gas was evolved and white solids precipitated, as the reaction proceeded. When the gas evolution was stopped, 236 g (1 mole) of glycidoxypropyltrimethoxysilane was added dropwise for 2 hrs. The solid was dissolved and the solution turned to light yellow. The solution was refluxed to complete the reaction for another 30 minutes. Gas chromatography analysis showed that no reactants were left. The solvent of hexane was evaporated to give the product.

The product contained about 10% of lithium salt of the product. Since the salt reacts with water to give the product back. It was not necessary to remove the salt from the product before the usage as the stabilizer for the inorganic silicated in antifreeze formulation.

| ir | OH | 3430 cm$^{-1}$ |
| --- | --- | --- |
|  | CN | 2170 cm$^{-1}$ |
| nmr($\delta$) | 0.43 (m, 2H), Si—CH$_2$ | |
|  | 1.57 (m, 4H), C—CH$_2$—C | |

-continued

| | | |
|---|---|---|
| | 2.65 (m, 1H), | C—CH—C<br>            \|<br>            O |
| | 3.52 (s, 9H), | CH$_3$O—Si |
| | 3.62 (m, 4H), | O—CH$_2$—C |
| | 3.72 (m, 1H), | Ph—CH— |
| | 4.65 (m, 1H), | OH |
| | 7.25 (m, 5H), | Ph |

EXAMPLE 20

The procedure of example 13 was repeated using the same number of moles of ethylacetoacetate instead of ethylcyanoacetate to prepare the stabilizer.

| ir | OH | 3452 cm$^{-1}$ |
|---|---|---|
| | C=O | 1725 cm$^{-1}$ |
| | | 1779 cm$^{-1}$ |
| nmr(δ) | 0.65 (m, 2H), Si—CH$_2$ | |
| | 1.22 (t, 3H), C—CH$_3$ | |

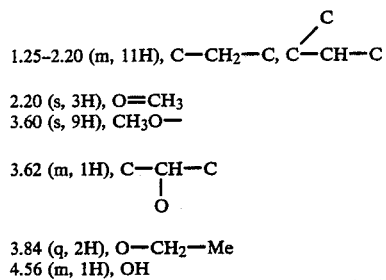

1.25–2.20 (m, 11H), C—CH$_2$—C, C—CH—C 2.20 (s, 3H), O=CH$_3$
3.60 (s, 9H), CH$_3$O—

3.62 (m, 1H), C—CH—C
                      |
                      O 3.84 (q, 2H), O—CH$_2$—Me
4.56 (m, 1H), OH

EXAMPLE 21

The product was prepared using the same procedure as described in Example 1 except n-butyllithium was replaced by same number of moles of methyllithium.

EXAMPLE 22

The product was prepared using the same procedure as described in Example 1 except n-butyllithium was replaced by methylmagnesium bromide in THF.

EXAMPLE 23

The product was prepared using the same procedure as described in Example 1 except n-butyllithium was replaced by phenyllithium.

EXAMPLE 24

The product was prepared using the same procedure as described in Example 1 except n-butyllithium was replaced by phenylmagnesium bromide in THF.

EXAMPLE 25

The product was prepared using the same procedure as described in Example 1 except n-butyllithium was replaced by t-butyllithium.

EXAMPLE 26

One equivalent of the product prepared in Example 1 is hydrolyzed by refluxing with five times of aqueous sodium hydroxide to give the corresponding siliconate having the following formular.

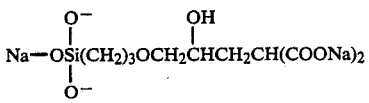

Na—OSi(CH$_2$)$_3$OCH$_2$CHCH$_2$CH(COONa)$_2$ with O$^-$, OH, O$^-$ substituents

EXAMPLE 27

In U.S. Pat. No. 4,367,154, there is disclosed an accelerated aging test method to estimate the gellation resistance of antifreeze compositions. The antifreeze samples were prepared according to GM 6038M of General Motor Co. The details of the compositions are 95.975% of ethylene glycol, 0.200% of sodium nitrate, 1.000% of sodium metaborate, 0.150% of sodium silicate, 0.200% of sodium tolyltriazole(50% aqueous solution), 0.450% of sodium orthophosphate, 0.20% of sodium hydroxide, 0.005% of pigment, and 2.000% of water.

The test was performed by placing a sample of the antifreeze composition in an oven controlled at 65° C. or 100° C. and measuring the number of days before the composition begins to gel. The gel stability of the sample at 65° C. and 100° C. and as well as those to which various stabilizing agents were added in the quantity of 100 ppm are presented in Table 1 wherein the time in days is the amount of time before the first visible formation of a gel was observed.

TABLE 1

| | Stabilizing Capability of Organosilanes | | |
|---|---|---|---|
| | | Stability(days) | |
| Ref. | Organosilane stabilizer | 65° C. | 100° C. |
| 1 | standard sample | 4 | 0.5 |
| 2 | (CH$_3$O)$_3$Si(CH$_2$)$_3$OCH$_2$CHCH$_2$CH(COOEt)$_2$ with OH | >30 | 3 |
| 3 | (CH$_3$O)$_3$Si(CH$_2$)$_2$CH—[ring]—CH—OH, CH—CH(COOEt)$_2$ | >30 | 5 |
| 4 | (CH$_3$O)$_3$Si(CH$_2$)$_3$CH$_2$CHCH$_2$CHCOOEt with OH and CN | 18 | 3 |

TABLE 1-continued

| | Stabilizing Capability of Organosilanes | Stability(days) | |
|---|---|---|---|
| Ref. | Organosilane stabilizer | 65° C. | 100° C. |
| 5 | (CH$_3$O)$_3$Si(CH$_2$)$_2$CH⟨ ⟩CH—OH<br>CH—CH(COOEt)$_2$<br>CN | >30 | >30 |
| 6 | (CH$_3$O)$_3$Si(CH$_2$)$_3$OCH$_2$CHCH$_2$CHCOOEt<br>OH    O=C—Me | >30 | >30 |
| 7 | (CH$_3$O)$_3$Si(CH$_2$)$_2$CH⟨ ⟩CH—OH<br>CH—CH(COOEt)$_2$<br>O=C—Me | 8 | 4 |
| 8 | O$^-$   OH<br>Na—OSi(CH$_2$)$_3$OCH$_2$CHCH$_2$CH(COONa)$_2$<br>O$^-$ | 18 | 8 |
| 9 | (CH$_3$O)$_3$Si(CH$_2$)$_3$OCH$_2$CHCH$_2$CHCOOMe<br>OH    Ph | >30 | >30 |
| 10 | (CH$_3$O)$_3$Si(CH$_2$)$_3$OCH$_2$CHCH$_2$CHCN<br>OH    Ph | 20 | 12 |

What is claimed is:

1. Organosilanes of the formula:

$$(RO)_3SiCH_2CH_2-R_1-\underset{R_3}{\overset{R_2}{\underset{|}{\overset{|}{CH}}}}$$

useful as a stabilizer of inorganic silicates in antifreezer/coolant formulations, wherein each R is independently an alkyl group of 1-4 carbon atoms, R$_1$ is selected from the group consisting of $$-CH_2OCH_2\underset{OH}{\underset{|}{CH}}CH_2-$$

and R$_2$ is -phenyl and R$_3$ is —CN.

2. A process for the preparation of an organosilane of the formula:

$$(RO)_3SiCH_2CH_2-R_1-\underset{R_3}{\overset{R_2}{\underset{|}{\overset{|}{CH}}}}$$

wherein R is an alkyl group of 1-4 carbon atoms, R$_1$ is selected from the group consisting of $$-CH_2OCH_2\underset{OH}{\underset{|}{CH}}CH_2- \text{ and } -CH\underset{}{\overset{}{\langle\ \rangle}}\begin{array}{c}CH-OH\\|\\CH-\end{array}$$

and R$_2$ is -Phenyl and R$_3$ is —CN, which comprises reacting glycidoxypropyltrialkoxysilane or beta-(3,4-epoxycyclohexyl) ethyltrimethoxysilane with an organic compound of the formula:

$$X-CH_2-Y$$

in the presence of a base catalyst at a temperature ranging between about 25° C. and about 200° C., wherein X and Y are identical or different and selected from the group consisting of -Phenyl and —CN.

3. The process as claimed in claim 2, wherein said base catalyst is selected from the group consisting of RLi, RMgX, M1OR, sodium hydride, and phenyllithium wherein R is an alkyl group of 1-4 carbon atoms, X is chlorine or bromine and M1 is sodium or potassium.

4. The process as claimed in claim 3, wherein said RLi is, selected from the group consisting of methyllithium, n-butyl-lithium, and t-butyllithium.

5. The process as claimed in claim 3, wherein said RMgX is selected from the group consisting of methyl magnesium chloride, and methyl magnesium bromide.

6. The process as claimed in claim 3, wherein said M1OR is sodium methoxide.

* * * * *

UNITED STATES PATENT AND TRADEMARK OFFICE
CERTIFICATE OF CORRECTION

PATENT NO. : 4,965,385
DATED : October 23, 1990
INVENTOR(S) : JUNG ET AL.

It is certified that error appears in the above—identified patent and that said Letters Patent is hereby corrected as shown below:

Column 11, line 50;

Claim 1, delete

" 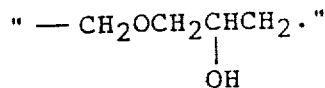 "

and insert

-- 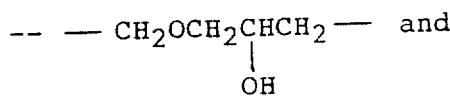 and 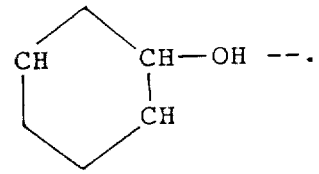 --.

Signed and Sealed this

Twenty-sixth Day of May, 1992

Attest:

DOUGLAS B. COMER

Attesting Officer     Acting Commissioner of Patents and Trademarks